United States Patent
Yoo et al.

(10) Patent No.: US 10,970,837 B2
(45) Date of Patent: Apr. 6, 2021

(54) AUTOMATED UNCERTAINTY ESTIMATION OF LESION SEGMENTATION

(71) Applicant: Siemens Healthcare GmbH, Erlangen (DE)

(72) Inventors: Youngjin Yoo, Princeton, NJ (US); Mariappan S. Nadar, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 148 days.

(21) Appl. No.: 16/355,881

(22) Filed: Mar. 18, 2019

(65) Prior Publication Data

US 2020/0302596 A1 Sep. 24, 2020

(51) Int. Cl.
*G06T 7/11* (2017.01)
*G06K 9/62* (2006.01)
*G06T 7/00* (2017.01)
*A61B 5/055* (2006.01)

(52) U.S. Cl.
CPC .......... *G06T 7/0012* (2013.01); *G06K 9/6293* (2013.01); *G06T 7/11* (2017.01); *A61B 5/055* (2013.01); *G06T 2207/10088* (2013.01); *G06T 2207/20076* (2013.01); *G06T 2207/20081* (2013.01); *G06T 2207/20128* (2013.01); *G06T 2207/20221* (2013.01); *G06T 2207/30016* (2013.01); *G06T 2207/30096* (2013.01)

(58) Field of Classification Search
None
See application file for complete search history.

(56) References Cited

U.S. PATENT DOCUMENTS

| 10,049,451 B2 | 8/2018 | Fisher | |
| 2017/0372193 A1* | 12/2017 | Mailhe | G06N 3/0472 |
| 2019/0392267 A1* | 12/2019 | Tang | G06T 7/11 |
| 2020/0160535 A1* | 5/2020 | Ali Akbarian | G06N 5/046 |

(Continued)

OTHER PUBLICATIONS

Guotai Wang et al: "DeepIGeoS: A Deep Interactive Geodesic Framework for Medical Image Segmentation", IEEE Transactions on Pattern Analysis and Machine Intelligence, Jan. 1, 2018 (Jan. 1, 2018), pp. 1-1. XP 055495101 / Jan. 1, 2018.

(Continued)

*Primary Examiner* — Idowu O Osifade

(57) ABSTRACT

Methods and systems are provided for automatically estimating image-level uncertainty for MS lesion segmentation data. A segmentation network is trained to segment MS lesions. The trained segmentation network is then used to estimate voxel level measures of uncertainty by performing Monte-Carlo (MC) dropout. The estimated voxel level uncertainty measures are converted into lesion level uncertainty measures. The information density of the lesion mask, the voxel level measures, and the lesion level measures is increased. A trained network receives input images, the segmented lesion masks, the voxel level uncertainty measures, and the lesion level uncertainty measures and outputs an image level uncertainty measure. The network is trained with a segmentation performance metric to predict an image level uncertainty measure on the segmented lesion mask that is produced by the trained segmentation network.

20 Claims, 6 Drawing Sheets

(56) References Cited

U.S. PATENT DOCUMENTS

2020/0167930 A1* 5/2020 Wang .................. G06T 7/0012

OTHER PUBLICATIONS

Mehta Raghav et al: "RS-Net: Regression-Segmentation 3D CNN for Synthesis of Full Resolution Missing Brain MRI in the Presence of Tumours", Sep. 12, 2018 (Sep. 12, 2018), Pervasive: International Conference on Pervasive Computing; [Lecture Notes in Computer Science; Lect.Notes Computer], Springer, Berlin, Heidelberg, pp. 119-129, XP047485121, / Sep. 12, 2018.

DeVries, Terrance, and Graham W. Taylor. "Leveraging Uncertainty Estimates for Predicting Segmentation Quality." arXiv preprint arXiv:1807.00502 (2018). pp. 1-9.

Nair, Tanya, et al. "Exploring uncertainty measures in deep networks for multiple sclerosis lesion detection and segmentation." International Conference on Medical Image Computing and Computer-Assisted Intervention. Springer, Cham, 2018.

Yoo, Youngjin, et al. "Deep learning of brain lesion patterns for predicting future disease activity in patients with early symptoms of multiple sclerosis." Deep Learning and Data Labeling for Medical Applications. Springer, Cham, 2016. 86-94.

* cited by examiner

AUTOMATED UNCERTAINTY ESTIMATION OF LESION SEGMENTATION

FIELD

The present embodiments relate to medical image acquisition and processing.

BACKGROUND

Multiple Sclerosis (MS) is an autoimmune disease that leads to lesions in the central nervous system. Progressive MS lesion formation often leads to cognitive decline and physical disability. Due to its sensitivity in detecting MS lesions, Magnetic Resonance Imaging (MRI) has become an effective tool for diagnosing MS and monitoring its progression. Manual assessment of each lesion in MR images is a tedious, demanding, and laborious task, and may also return poor results and poor reproducibility.

Automatic segmentation provides an alternative to manual segmentation. Automatic segmentation, however, still presents challenges. Progression of MS lesions shows considerable variability and temporal changes in shape, location, and area between patients and even for the same patient. This makes the automatic segmentation of MS lesions a challenging problem and more than mere automation of what is done by a human. Deep learning techniques have been used for automated lesion segmentation, but the segmentation performance is still limited due to the variability in lesion shape and size across patients.

SUMMARY

By way of introduction, the preferred embodiments described below include methods and systems for automatically estimating image level uncertainty on MS lesion segmentation. Automated uncertainty estimation of MS lesion could be helpful to efficiently allow subsequent revisions and thus accelerate adoption of deep learning based segmentation system into clinical practice. The uncertainty measurement provided may be used to inform clinicians of segmentation results that need further revision. Embodiments incorporate lesion level uncertainty measures as an input channel. To overcome overfitting and instability in model training that are caused by data sparsity in voxel level and lesion level uncertainty maps, embodiments increase the information density of the uncertainty maps to reflect unique characteristics of MS lesions visible on MRI scans.

In a first aspect, a method is provided for estimating uncertainty measurements on lesion segmentation. MRI data is acquired by a magnetic resonance imaging device. Segmented lesion data is generated by a first trained network from the MRI data. Voxel level measures of uncertainty are estimated from the segmented lesion data. Lesion level measures of uncertainty are generated from the voxel level measures of uncertainty. A second trained network predicts an image level uncertainty measure for the segmented lesion data, the second trained network configured to receive the MRI data, the segmented lesion data, the voxel level measures of uncertainty, and the lesion level uncertainty measures as input data and to predict the image level uncertainty measure.

In a further aspects the image processor increase information density of the segmented lesion data, the voxel level measures of uncertainty, and the lesion level measures of uncertainty. Increasing the information density may include increasing, by the image processor, information density by Euclidean distance transform for the segmented lesion data; and increasing, by the image processor, information density by geodesic distance transform for the voxel level measures of uncertainty and the lesion level measures of uncertainty. Generating the lesion level measures of uncertainty may include merging the voxel level measures of uncertainty into lesion level uncertainty measures by taking the log-sum of the voxel level measures of uncertainty. Estimating voxel level measure of uncertainty may utilize MC dropout. Estimating the voxel level measures of uncertainty may utilize maximum soft-max probability. The first trained network may be a convolutional neural network trained to perform segmentation on input data. The second trained network may be trained using the same training data set as the first trained network. The uncertainty measure may be provided to inform a clinician of segmentation results that require further revision.

In a second aspect, a method is provided for training a network for predicting image level uncertainty. Training data is acquired that comprises an input image, a predicted segmentation mask generated by a trained segmentation network, a voxel level uncertainty map, and a lesion level uncertainty map. The training data is input into the network. A segmentation performance metric is output. The segmentation performance metric is compared against a ground truth performance metric. Weights are adjusted in the network as a function of the comparison. A trained network is output.

In a further aspect, inputting, outputting, comparing, and adjusting are repeated multiple times until convergence of a gradient to a solution. The segmentation network is trained using the training data. The information density of the predicted segmentation mask, the voxel level uncertainty map, and the lesion level uncertainty map may be increased prior to inputting the training data into the network. The network may be a convolutional neural network.

In a third aspect, a system is provided for predicting image level uncertainty. The system includes a trained segmentation network, an image processor, and a trained network. The trained segmentation network is configured to input MRI data and output segmented lesion data. The image processor is configured to generate a voxel level uncertainty map, and a lesion level uncertainty map from the segmented lesion data. The trained network is configured to receive the segmented lesion data, the input MRI data, the voxel level uncertainty map, and the lesion level uncertainty map and to predict an image level uncertainty measure.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION

Methods and systems are provided for automatically estimating image-level uncertainty for MS lesion segmentation data. A segmentation network is trained to segment MS lesions. The trained segmentation network is then used to estimate voxel level measures of uncertainty by performing Monte-Carlo (MC) dropout. The estimated voxel level uncertainty measures are converted into lesion level uncertainty measures. The information density of the lesion mask, the voxel level measures, and the lesion level measures is increased. A trained network receives input images, the segmented lesion masks, the voxel level uncertainty measures, and the lesion level uncertainty measures and outputs an image level uncertainty measure. The network is trained with a segmentation performance metric to predict an image level uncertainty measure on the segmented lesion mask that is produced by the trained segmentation network.

Automated lesion segmentation is desired in clinical practice as manual segmentation requires time-consuming and expensive labor. However, performance of automated methods may not be accurate enough for clinical adoption. An uncertainty measurement may be used to inform clinicians of segmentation results that need further revision. To efficiently provide the image level uncertainty, embodiments incorporate the lesion level uncertainty measure as an input channel. The lesion level uncertainty measure includes crucial pathological information that is highly correlated to the image level uncertainty. In addition, to overcome overfitting of the model and instability in the model training that is caused by data sparsity in the voxel level and lesion level uncertainty measures, embodiments increase the information density of the uncertainty measures to reflect the unique characteristics of MS lesions visible on MRI scans.

In the embodiments described below, the imaging system is a magnetic resonance (MR) imaging system. Other imaging systems may be used such as computed tomography (CT) or ultrasound. In addition, the examples below describe the embodiment using a scan of a patient's brain. Other regions or organs of a patient may be scanned, for example, the nerves in any part of the body, lungs, breast, or heart.

Figure 1:
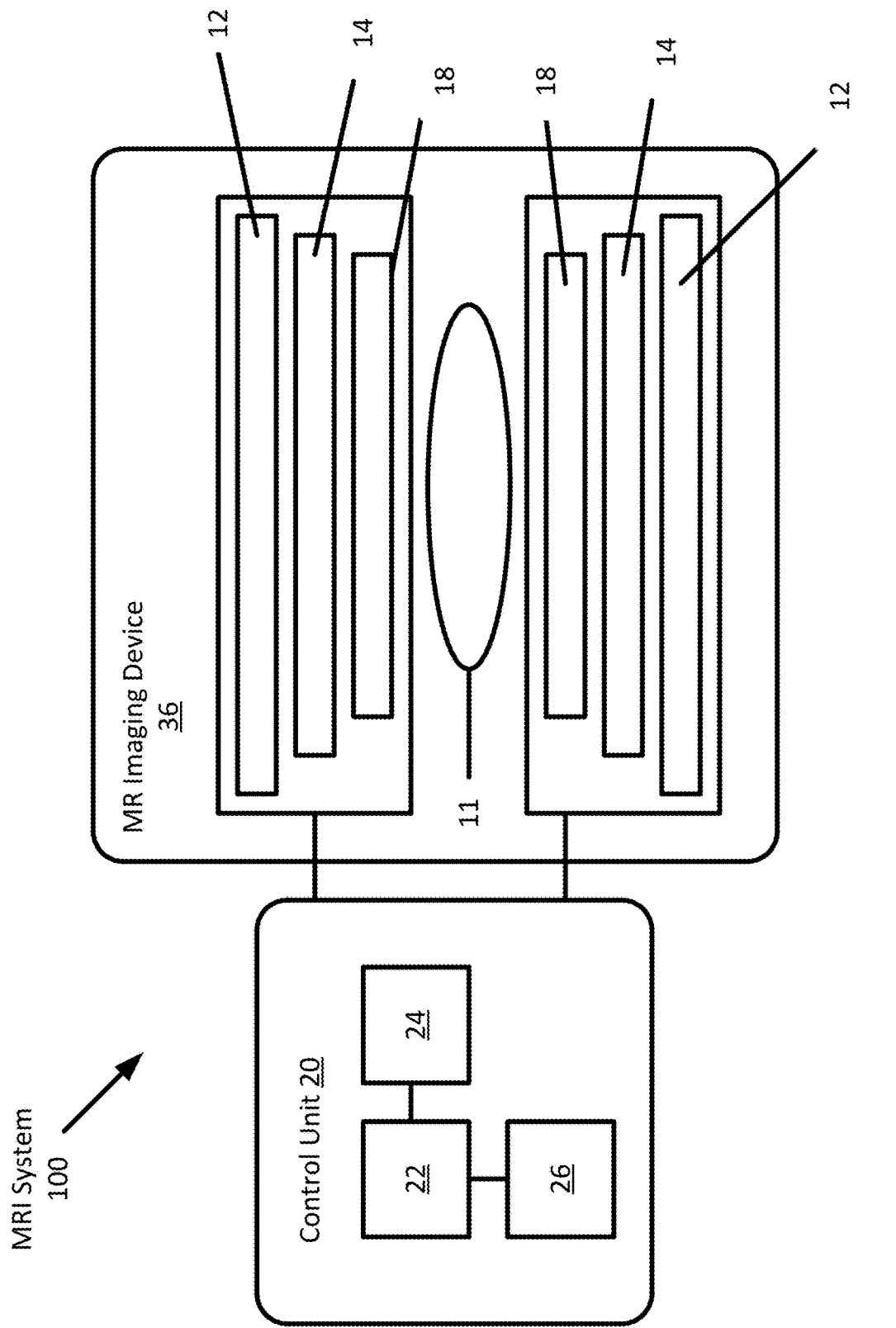
FIG. 1 depicts an example MR system.

FIG. 1 depicts an MR system 100 for acquisition of frequency domain components representing MR data for storage in a storage array. The MR system 100 includes a control unit 20 configured to process the MR signals and generate images of the body for display to an operator. The control unit 20 may store the MR signals and images in a memory 24 for later processing or viewing. The control unit 20 may include a display 26 for presentation of images to an operator. The MR scanning system 100 is only exemplary, and a variety of MR scanning systems may be used to collect the MR data.

In the MR system 100, magnetic coils 12 create a static base or main magnetic field $B_0$ in the body of patient 11 or an object positioned on a table and imaged. Within the magnet system are gradient coils 14 for producing position dependent magnetic field gradients superimposed on the static magnetic field. Gradient coils 14, in response to gradient signals supplied thereto by a gradient and control unit 20, produce position dependent and shimmed magnetic field gradients in three orthogonal directions and generate magnetic field pulse sequences. The shimmed gradients compensate for inhomogeneity and variability in an MR imaging device magnetic field resulting from patient anatomical variation and other sources.

The control unit 20 may include a RF (radio frequency) module that provides RF pulse signals to RF coil 18. The RF coil 18 produces magnetic field pulses that rotate the spins of the protons in the imaged body of the patient 11 by ninety degrees or by one hundred and eighty degrees for so-called "spin echo" imaging, or by angles less than or equal to 90 degrees for "gradient echo" imaging. Gradient and shim coil control modules in conjunction with RF module, as directed by control unit 20, control slice-selection, phase-encoding, readout gradient magnetic fields, radio frequency transmission, and magnetic resonance signal detection, to acquire magnetic resonance signals representing planar slices of the patient 11.

In response to applied RF pulse signals, the RF coil 18 receives MR signals, e.g. signals from the excited protons within the body as the protons return to an equilibrium position established by the static and gradient magnetic fields. The MR signals are detected and processed by a detector within RF module and the control unit 20 to provide an MR dataset to a processor 22 for processing into an image. In some embodiments, the processor 22 is located in the control unit 20, in other embodiments, the processor 22 is located remotely. A two or three-dimensional k-space storage array of individual data elements in a memory 24 of the control unit 20 stores corresponding individual frequency components including an MR dataset. The k-space array of individual data elements includes a designated center, and individual data elements individually include a radius to the designated center.

A magnetic field generator (including coils 12, 14 and 18) generates a magnetic field for use in acquiring multiple individual frequency components corresponding to individual data elements in the storage array. The individual frequency components are successively acquired using a Cartesian or other spatial acquisition strategy as the multiple individual frequency components are sequentially acquired during acquisition of an MR dataset. A storage processor in the control unit 20 stores individual frequency components acquired using the magnetic field in corresponding individual data elements in the array. The row and/or column of corresponding individual data elements alternately increases and decreases as multiple sequential individual frequency components are acquired. The magnetic field generator acquires individual frequency components in an order corresponding to a sequence of substantially adjacent individual data elements in the array, and magnetic field gradient change between successively acquired frequency components is substantially minimized.

One use of MRI is for detecting MS lesions in a patient. MRI is a non-invasive imaging technique for studying the brain as MRI is highly sensitive in detecting MS plaques and may provide quantitative assessment of inflammatory activity and lesion load. MRI protocols such T1-weighted (T1-w), T2-weighted (T2-w), PD-weighted (PD-w), and attenuated inversion recovery T2 (T2-FLAIR) sequences may be used to detect MS lesions. MS lesions exhibit hyperintensities in T2-w, PD-w and T2-FLAIR MRI sequences, and hypo-intensities in T1-w MRI sequences, with respect to normal intensities.

In previous approaches, lesions were visually identified in MR images and measured by neuroradiologists. Manual segmentation of MS lesions is a time-consuming and tedious process. In addition, manual segmentation is subjective and is prone to human errors. Automated lesion segmentation and identification is not subjective and not prone to human errors. Automated lesion segmentation, however, also has drawbacks. Automated lesion segmentation in MS is a challenging task for various reasons: (1) the lesions are highly variable in terms of size and location, (2) lesion boundaries are often not well defined, and (3) clinical quality FLAIR images may possess low resolution and often have imaging artifacts. In addition, automated lesion segmentation depends on human input to train the segmentation model and there is very high inter-rater variability even with experienced raters. The problems are accentuated by the fact that MRI does not have any uniform intensity scale (like CT); acquisition of images in different scanners and with different contrast properties may therefore add to the complexity of segmentation.

Many automated lesion segmentation methods have been proposed in the past. There are usually two broad categories of segmentations, supervised and unsupervised. Unsupervised lesion segmentation methods rely on intensity models of brain tissue, where image voxels contain high intensities. Supervised lesion segmentation methods make use of atlases or templates, that typically include multi contrast MR images and their manually delineated lesions. Deep learning approaches have shown success in the segmentation of large lesions and recent work has shown how using a tissue prior or lesion prior may improve detection for medium and small lesions. However, current deep learning methods have not yet been shown to outperform other machine learning methods in the detection of small lesions, leading to potential errors in patient lesion counts that may have serious consequences in clinical trials. Moreover, many deep learning methods may produce predictors with deterministic outcomes. An alternative, traditional Bayesian machine learning provides not only a prediction, but also an uncertainty about it, through a probability density over outcomes. An example is a Bayesian Neural Network (BNN), that attempts to learn a distribution over each of the network's weight parameters. Such a network would be able to produce a distribution over the output for any given input, thereby naturally producing uncertainty estimates. However, Bayesian inference is computationally intractable for the models in practice. Different efforts have been used to provide approximations of Bayesian neural networks that are easier to train. Recent efforts include Monte-Carlo (MC) Dropout, Multiplicative Normalizing Flows, and Stochastic Batch Normalization. The methods have been shown to be capable of producing uncertainty estimates, although with varying degrees of success. The main disadvantage with the BNN approximations is that the methods require sampling in order to generate the output distributions. As such, uncertainty estimates are often time-consuming or resource intensive to produce, often requiring 10 to 100 forward passes through a neural network in order to produce useful uncertainty estimates at inference time.

An alternative to BNNs is deep ensembles, which propose a frequentist approach to the problem of uncertainty estimation by training many models and observing the variance in their predictions. However, this technique is still resource intensive, as the technique requires inference from multiple models in order to produce the uncertainty estimate.

Another method includes computing voxel wise uncertainty estimates based on MC dropout within the context of a three-dimensional convolutional neural network (CNN). Lesion uncertainty estimates are subsequently computed by accumulating the voxel uncertainty measures within detected lesions. Segmented lesions are further filtered by another chosen threshold based on voxel and lesion uncertainties to improve the accuracy. Another method proposes a two-stage deep learning architecture to produce an image-level uncertainty on segmentation results. The first network is trained to produce a segmentation result and voxel uncertainty estimates using MC dropout, and the second network is trained using an input image to produce an image-level uncertainty estimate. The methods and networks provide an image level uncertainty estimate, but may be unreliable and produce false positives.

Embodiments provide systems and methods for automated uncertainty estimation of lesion segmentation. A segmentation network is configured to receive training data and trained to segment focal MS lesions. The segmentation network may be any architecture such as a U-net. The trained segmentation network is then used to estimate voxel level measures of uncertainty by performing MC dropout. The estimated voxel level uncertainty measures are merged into lesion level uncertainty measures by taking the log-sum of voxel level uncertainties.

Embodiments also include a module or processor that is configured to increase information density by Euclidean distance transform (EDT) for the lesion mask that is a binary volume and geodesic distance transform (GDT) for the voxel level and lesion level uncertainties that are grey level volumes. Embodiments also include a neural network that is configured to receive input images, lesion masks, voxel- and lesion level uncertainty maps, that are transformed as described above, as input training data, and to be trained with segmentation performance metrics such as a DICE similarity score to predict an image level uncertainty measure on a segmented lesion mask that is produced by the trained segmentation network.

Embodiments provide a deep learning approach for creating a network that cannot be practically performed manually. The deep learning approach is different than the approach taken by a human, such as through the definition of the architecture used. The disclosed networks may be implemented to computationally facilitate processing of medical imaging data and consequently improving and optimizing medical diagnostics. Embodiments provide an improvement to the efficiency of managing MS patients by reducing the amount of time required for examining MRI scans of MS patients and to provide enhanced disease diagnosis and prognosis. The disclosed embodiments may be implemented to computationally facilitate processing of medical imaging data and consequently improving and optimizing medical diagnostics. By using an automated workflow, errors in the diagnosis are diminished and outcomes are improved. The use of an automated segmentation is efficient in that a correct number of resources are used to acquire the needed medical images for diagnosis. The use of an automated segmentation process further limits errors by removing user errors and decisions from the process. The automated segmentation process is improved by the inclusion of the uncertainty measures that allow a technician to identify any errors or issues with the resulting segmentation. The generated patient-specific process saves time for both the patient and any personal that reviews the images.

Figure 2:
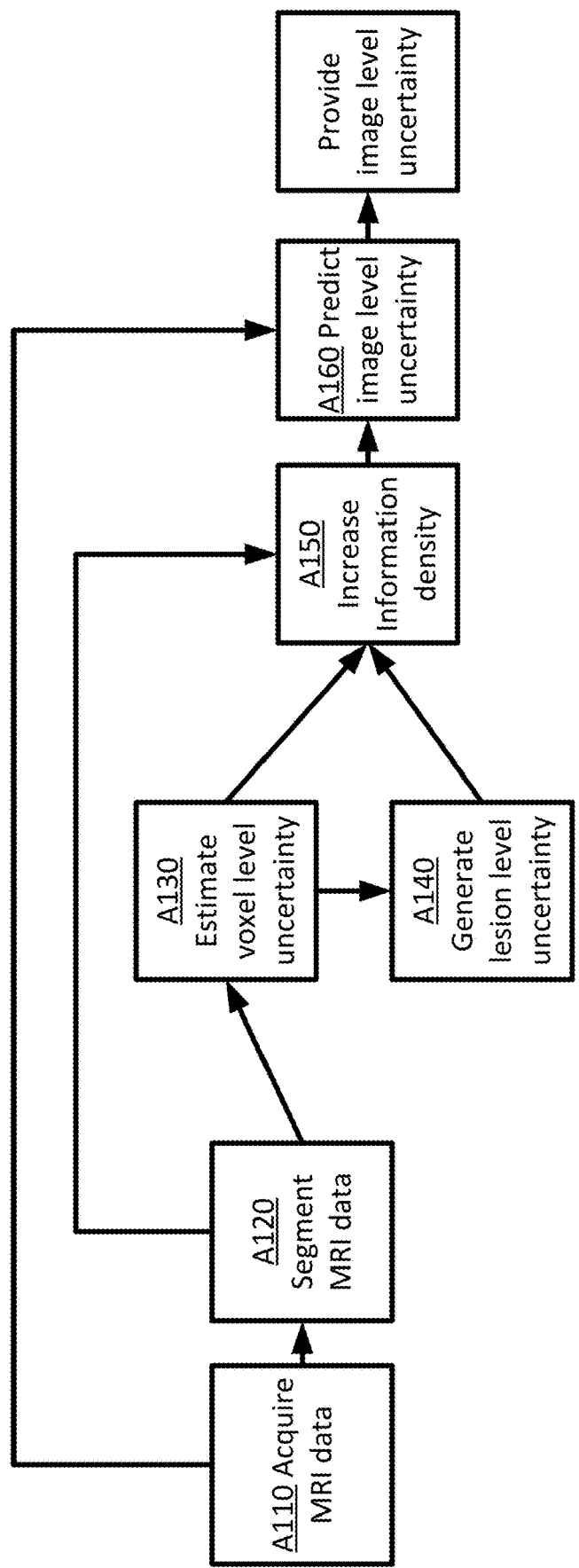
FIG. 2 depicts an example method for estimating uncertainty measures for lesion segmentation.

FIG. 2 depicts an example flowchart for providing automated uncertainty estimation of lesion segmentation from MRI images of multiple sclerosis patients. During application, the method provides an uncertainty measure that may be used by a technician or application to determine if the segmented MRI data is of a certain quality. The acts are performed by the system of FIG. 1 or 6, other systems, a workstation, a computer, and/or a server. Additional, different, or fewer acts may be provided. The acts are performed in the order shown (e.g., top to bottom) or other orders. The segmentation of the acquired MR data and analysis of the resulting segmentation data may be performed by networks or models trained using machine learning techniques. The networks or models may be trained prior to the act of FIG. 2. Training data may be acquired and used to configure the network or models. The networks or models may be updated as new training data is acquired or changes are made to the system. In an example, the trained segmentation network is applied at act A120 but may be trained at a prior point in time using machine learning techniques.

At act A110, MR data is acquired. The MR data may be acquired directly using an MRI system or from memory. As depicted and described in FIG. 1 above, MR data may be acquired using MR scanners. For example, gradient coils, a whole-body coil, and/or local coils generate a pulse or scan sequence in a magnetic field created by a main magnet or coil. The whole-body coil or local coils receive signals responsive to the re-orientation of molecules shifted due to the scan sequence. In an embodiment and used as an example below, MR data may represent image data for a brain of a patient. Different objects, organs, or regions of a patient may also be scanned.

MR data may be k-space data or image data. Image data may be MR data after Fourier transform into object space. The image data may be at any point after transform, so may be scalar values or may be formatted as RGB values for a display screen. MR data or image data may be scan data to be used to generate an image on a display. MR data may be data being processed to generate an image, data formatted for display, or data that has been used to display. MR data may be data with no or some image processing.

In an embodiment, the MR data may represent a volume. Three-dimensional datasets are obtained. As k-space data, information content may be provided that is responsive to a three-dimensional distribution of locations, but the data itself does not directly represent the locations prior to transform. In alternative embodiments, two-dimensional datasets representing or responsive to tissue in planes are obtained. In other embodiments, sequences of MR data responsive to the same tissue over time are acquired for training. Alternative methods may be used to acquire the MR data. The MR data may be acquired remotely from the server or workstation. The MR data may be stored locally onsite or offsite, for example in the cloud.

MR data includes both raw MR data and processed MR data. Processed MR data may include image and volume data. MR data may include 2D images, sequences of 2D images, 3D volumetric imagery, or sequence of 3D volumetric imagery. If the MR data is defined in 3D space (e.g., obtained from a series of MR images), each image "slice" may be provided individually in a "slice-by-slice" manner. Alternatively, the MR data may be acquired as 3D volumetric data directly. The examples described herein use three-dimensional MR data referred to as volumes. Additionally, the terms MR data and volume may be used interchangeably in that the MR data represents at least one volume. Volumes are encoded using an array of elements referred to as voxels. A voxel represents a value on a regular or irregular grid in three-dimensional space. Two-dimensional MR data may be encoded using a bitmap of pixels.

At act A120, the image processor 22 segments the MR data using a trained segmentation network. The MR data may be segmented using any segmentation method. Segmentation is the process of dividing an input into different parts or sections, e.g. for medical imaging, delineating the boundaries, or contours, of various tissues or structures in the body. Segmentation may also include classification. Classification assigns a label to the MR data, e.g. normal or abnormal, level of severity, a diagnosis, or type of tissue.

Classification may assign to each element in the image a tissue class when the classes are defined in advance. In the case of brain MR, for tissue classification, image elements may be classified into one or more of three main tissue types: white matter (WM), gray matter (GM), and cerebrospinal fluid (CSF). White matter lesions in MS may be detected with standard magnetic resonance imaging (MRI) acquisition protocols without contrast injection. For example, with T2-w FLAIR (Fluid attenuated inversion recovery) imaging sequences, most lesions appear as bright regions in MR images or volumes that helps its automatic segmentation. Classification of the tissue types requires segmentation of the MR data into different parts. Image segmentation may be performed on two dimensional images, sequences of two-dimensional images, three-dimensional volume, or sequences of three-dimensional volumes. If the data is defined in three-dimensional space (e.g., obtained from a series of MR images), each image slice may be segmented individually in a slice-by-slice manner. The two-dimensional slices are then connected into a 3D volume or a continuous surface. The segmentation network is trained using machine learning techniques to output segmented data. The segmented data may be split into masks that include data for different classified pixels or voxels. For example, there may be two masks, one for suspected lesions and one for everything else.

At act A130, the image processor 22 estimates voxel level measures of uncertainty by performing MC dropout. The voxel level measures may include estimates and/or values for each voxel in the segmented MR data. The collection of voxel level measures may be stored or visualized as a voxel feature map. Dropout is a technique used to avoid overfitting by randomly sampling the outputs of each layer, which provides the effect of thinning the network during training. MC-dropout models epistemic uncertainty that is the uncertainty associated with the model parameters. MC-dropout approximates a BNN by sampling from a neural network trained with dropout at inference time in order to produce a distribution over the outputs. Following the approach used for BNN, dropout may be applied after each convolution block of the U-net architecture. During run time, the segmentation network is sampled T times and then the average SoftMax probability is calculated over all the samples to approximate the MC integration. Model uncertainty is estimated by calculating the entropy of the averaged probability vector across the class dimension. Possible alternatives may be to use maximum SoftMax probability or mutual information for estimating voxel level uncertainty. The SoftMax probability may be obtained without performing any additional processing. To calculate the maximum SoftMax probability, the maximum is calculated across the class dimension of the SoftMax output from the network. For segmentation, this is done per output pixel in order to obtain an uncertainty map that is of the same resolution as the input image.

At act A140, the image processor 22 generates lesion level uncertainty values from the voxel level values of uncertainty. The estimated voxel level uncertainty measures are merged into lesion level uncertainty measures by taking the log-sum of voxel level uncertainties of the voxels for segmented lesions. The lesion level measures may include estimates and/or values for each identified lesion in the segmented MR data. The collection of lesion level measures may be stored or visualized as a lesion feature map. For a candidate (1) that includes voxels p . . . q, the lesion uncertainty Um(1) is computed from the voxel uncertainties as:

$$U_m(l) = \Sigma_{i=p}^{q} \log(U_m(i)).$$

Taking the log-sum of the voxel level uncertainties reflects the simplifying assumption that neighboring voxels are conditionally independent, given that the neighboring voxels are part of 1. To make the uncertainties comparable through a single threshold value, the values Um(1) are rescaled to [0; 1] by subtracting by a minimum lesion uncertainty and dividing by the range. This is performed separately for each measure m. The lesion level uncertainties and voxel level uncertainties may be stored as a grey level feature map with values for each pixel of the map given a value that describes the uncertainty level.

Figure 3:
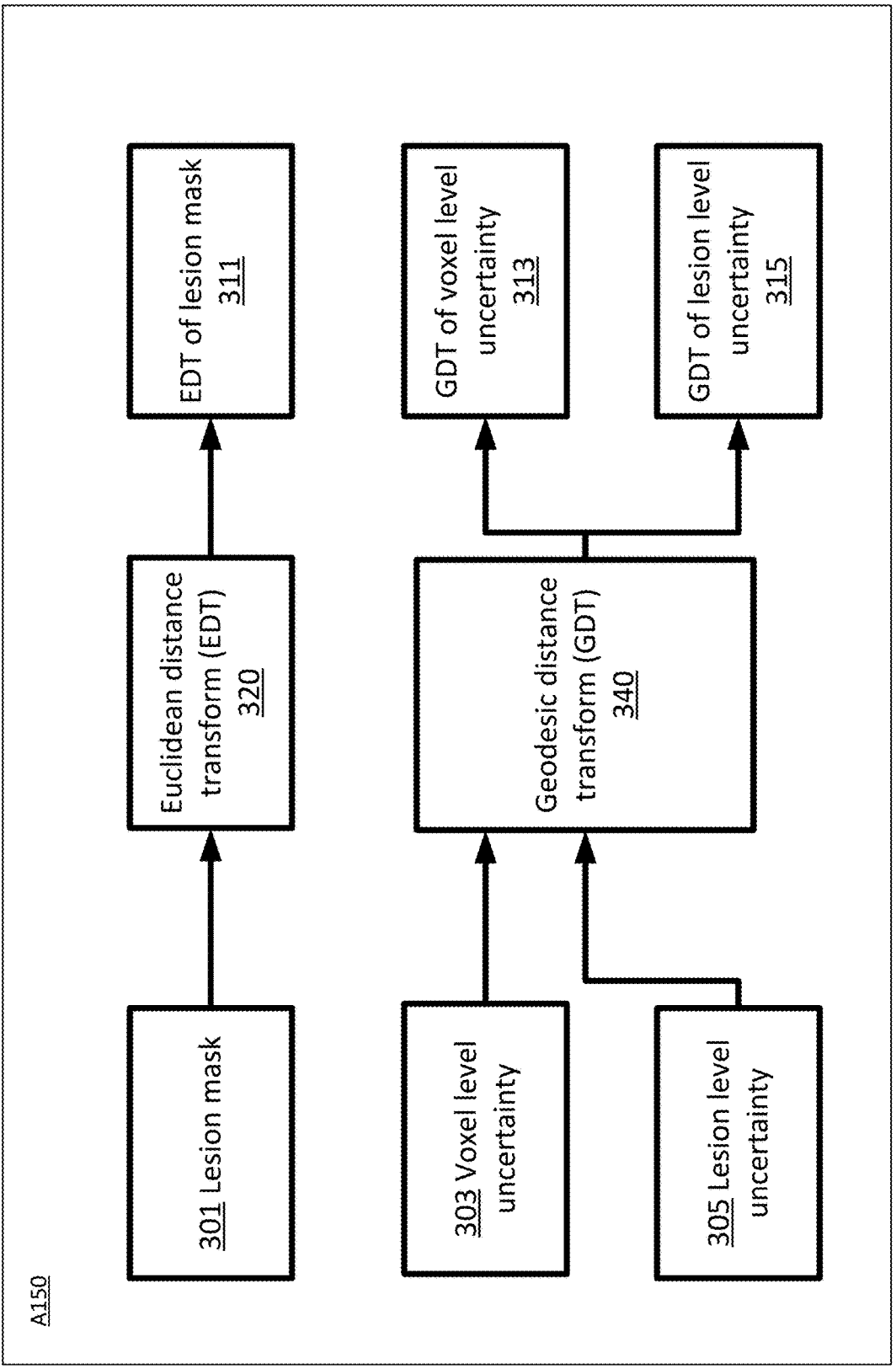
FIG. 3 depicts an example method for increasing information density.

At act A150, the image processor 22 increases the information density of the segmented lesion mask generated at act A120, the voxel level measures of uncertainty generated at act A130 and the lesion level measures of uncertainty generated at act A140. In an embodiment, the image processor 22 increases the information density by EDT for the lesion mask and by GDT for the voxel level and lesion level uncertainties. FIG. 3 depicts the transformation of the data. In FIG. 3, the inputs include the lesion mask 301, the voxel-level uncertainty 303, and the lesion level uncertainty 305. The outputs are the EDT of the lesion mask 311, the GDT of the voxel level uncertainty 313, and the GDT of the lesion level uncertainty 315.

Figure 4:
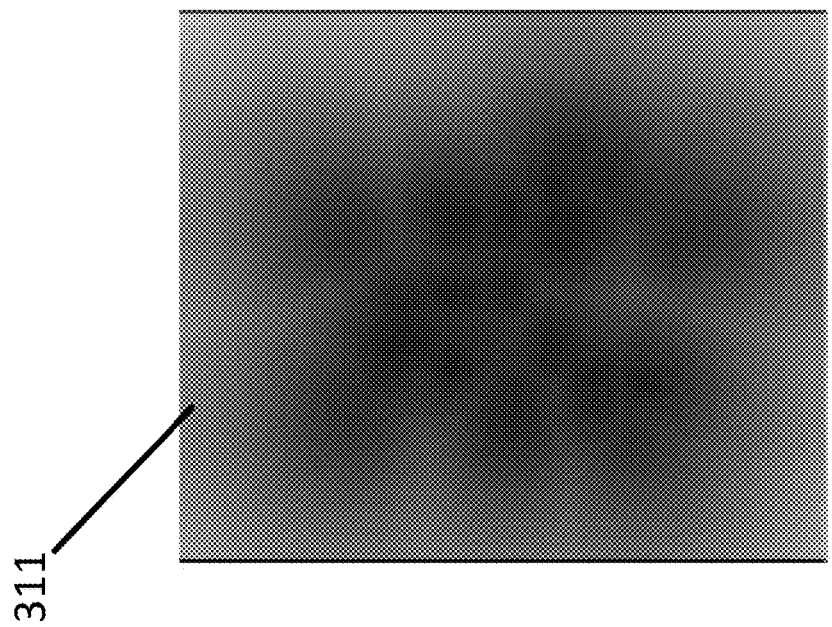
FIG. 4 depicts an example of a Euclidian distance transform.
Figure 4:
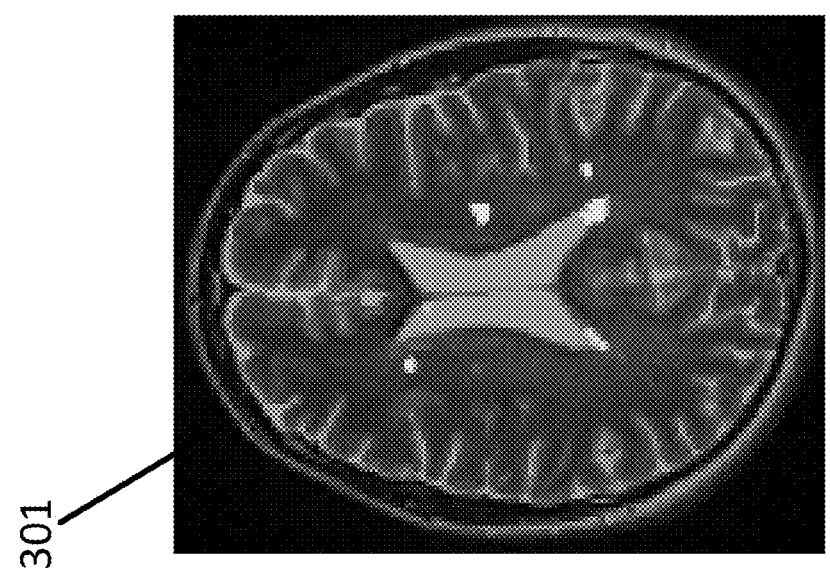

The distance transform algorithm inputs a binary image, for example, the lesion mask 301 where the pixels are either 0 or 1, and outputs a distance map. The distance map includes the same dimensions of the input image and each pixel contains for example, the Euclidean distance, to the closest obstacle pixel (e.g. border pixel). The distance transform is typically only applied to binary images. The segmentation masks 301 generated at act A120 are each a binary image, for example with white representing normal tissue and black representing predicted lesions. The result of the transform is a gray level image that looks similar to the input segmentation mask, except that the gray level intensities of points inside non-lesioned regions are changed to show the distance to the closest boundary from each point. FIG. 4 depicts one example of GDT. FIG. 4 depicts the lesion mask 301 and the EDT of the lesion mask 311.

Different transform algorithms that use different distance metric calculations may be used. The Euclidean distance represents the straight-line distance between two points. If the two pixels that have coordinates $(x_1, y_1)$ and $(x_2, y_2)$, then the Euclidean distance is given by:

$$D_{Euclid} = \sqrt{(x_2-x_1)^2 + (y_2-y_1)^2}$$

Another distance calculation is the city distance that is also known as the Manhattan distance. This metric assumes that in going from one pixel to the other it is only possible to travel directly along pixel grid lines. Diagonal moves are not allowed. Therefore the 'city block' distance is given by:

$$D_{City} = |x_2-x_1| + |y_2-y_1|$$

Another distance calculation is the chessboard distance. This metric assumes that moves may be made on the pixel grid as a King making moves in chess, e.g. a diagonal move counts the same as a horizontal move. The metric is given by:

$$D_{Chess} = \max(|x_2-x_1|, |y_2-y_1|)$$

GDT is another distance transform that may be used to calculate the distance between two vertices. The geodesic distance is the distance between two vertices in a graph may be calculated by the number of edges in a shortest path (also called a graph geodesic) that connect the two vertices. The GDT may be weighted by uncertainty.

At act A160, the image processor 22 predicts, using a trained network, an image level uncertainty measure for the segmented MR data. The trained network is configured to receive input images (MR data from A110), lesion mask(s) 311 (from A120), voxel and lesion level uncertainty maps (from A130, A140), that are transformed as described above (at A150), as input data, and to predict an image level uncertainty measure.

The trained network may be a CNN network, for example, a VGG-style CNN. A DenseNet or other network arrangements may also be used for the trained networks or other trained networks described above in Act A120 for segmentation or classification. A DenseNet connects each layer in a network to every other layer in a feed-forward fashion. For each layer in the DenseNet, the feature-maps of all preceding layers are used as inputs, and the output feature-map of that layer is used as input into all subsequent layers. In the DenseNet, for each layer, the feature maps of all preceding layers are used as inputs, and its own feature maps are used as inputs into all subsequent layers. To reduce the size of the network, the DenseNet may include transition layers. The layers include convolution followed by average pooling. The transition layers reduce height and width dimensions but leave the feature dimension the same. The neural network may instead be configured as a U-net. The U-Net is an autoencoder in which the outputs from the encoder-half of the network are concatenated with the mirrored counterparts in the decoder-half of the network. Skip connections prevent the middle of the network from becoming a bottleneck.

Deep architectures include CNN or deep belief nets (DBN), but other deep networks may be used. CNN learns feed-forward mapping functions while DBN learns a generative model of data. In addition, CNN uses shared weights for all local regions while DBN is a fully connected network (e.g., including different weights for all regions of an image). The training of CNN is entirely discriminative through back-propagation. DBN, on the other hand, employs the layer-wise unsupervised training (e.g., pre-training) followed by the discriminative refinement with back-propagation if necessary. In an embodiment, the arrangement of the trained network is a fully convolutional network (FCN). Alternative network arrangements may be used, for example, a 3D Very Deep Convolutional Networks (3D-VGGNet). VGGNet stacks many layer blocks containing narrow convolutional layers followed by max pooling layers. A 3D Deep Residual Networks (3D-ResNet) architecture may be used. A Resnet uses residual blocks and skip connections to learn residual mapping.

Each of the types of neural networks are defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous and/or subsequent layer or unit. Skip connections may be used, such as a layer outputting to the sequentially next layer as well as other layers. Rather than pre-programming the features and trying to relate the features to attributes, the deep architecture is defined to learn the features at different levels of abstraction based on the input data. The features are learned to reconstruct lower level features (i.e., features at a more abstract or compressed level). For example, features for reconstructing an image are learned. For a next unit, features for reconstructing the features of the previous unit are learned, providing more abstraction. Each node of the unit represents a feature. Different units are provided for learning different features.

Various units or layers may be used, such as convolutional, pooling (e.g., max-pooling), deconvolutional, fully connected, or other types of layers. Within a unit or layer, any number of nodes is provided. For example, 100 nodes are provided. Later or subsequent units may have more, fewer, or the same number of nodes. In general, for convolution, subsequent units have more abstraction. For example, the first unit provides features from the image, such as one node or feature being a line found in the image. The next unit combines lines, so that one of the nodes is a corner. The next unit may combine features (e.g., the corner and length of lines) from a previous unit so that the node provides a shape indication. For transposed-convolution to reconstruct, the level of abstraction reverses. Each unit or layer reduces the level of abstraction or compression.

The trained network is trained to predict the quality of the segmentation, given the original input image, as well as the predicted segmentation mask 301 from the segmentation network and uncertainty maps. The segmentation quality measurement can be any segmentation-based evaluation metric, or even multiple metrics predicted simultaneously. Different metrics that may be used may include DICE, Jaccard, true positive rate, true negative rate, modified Hausdorff, volumetric similarity, or others. DICE is a measure of the comparison between two different images or sets of values. The Jaccard index (JAC) between two sets is defined as the intersection between them divided by their union. True Positive Rate (TPR), also called Sensitivity and Recall, measures the portion of positive voxels in the ground truth that are also identified as positive by the segmentation being evaluated. Analogously, True Negative Rate (TNR), also called Specificity, measures the portion of negative voxels (background) in the ground truth segmentation that are also identified as negative by the segmentation being evaluated. The segmentation quality measurement may be provided to a user along with the MR data that is segmented. The segmentation quality measurement may be compared against a threshold measurement. If the segmentation quality measurement does not meet or surpass the threshold, the MR data and the segmented data may be flagged for review or reprocessed.

To train the network, ground truth segmentation quality labels are used. The ground truth segmentation quality labels may be manually generated or automatically generated using different techniques. The unlabeled training data is input into the network that generates an outcome that is compared against associated labeled training data. Using backpropagation and a gradient, the network adjusts internal parameters based on the comparison. The process is repeated until the network may no longer be improved or a set point is reached. The training set for may be the same one as used to train the segmentation network, or a separate holdout set, or a combination of the two. In the case that segmentation network performs very well on the training set, a holdout set may be necessary, as the lack of examples of poor segmentations will bias the trained network towards always predicting that the segmentation is good.

Figure 5:
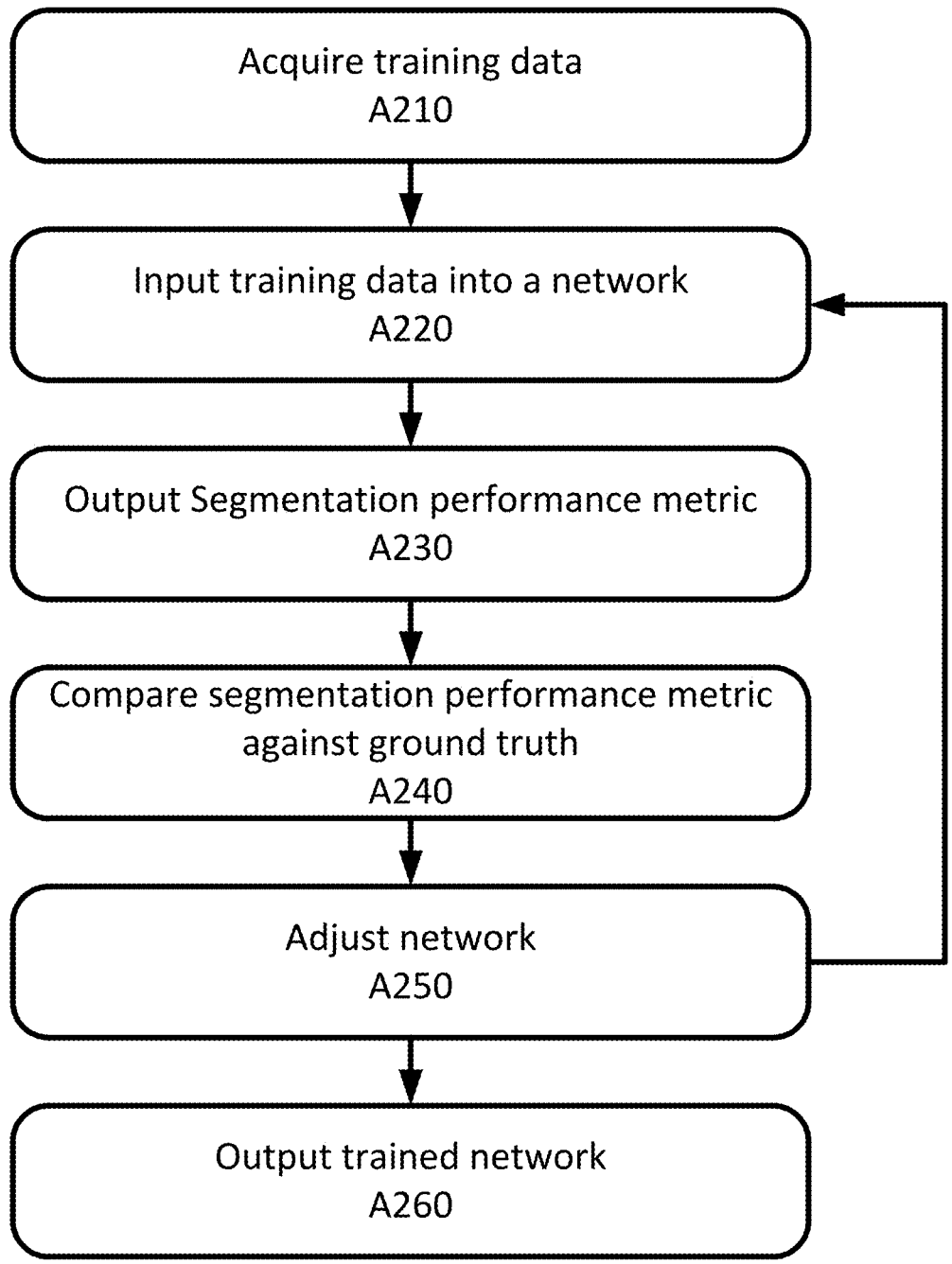
FIG. 5 depicts an example method for training a network to generate estimates of uncertainty for lesion segmentation.

FIG. 5 depicts a workflow for training a network to generate image level uncertainty measures. The acts are performed by the system of FIG. 1 or 6, other systems, a workstation, a computer, and/or a server. Additional, different, or fewer acts may be provided. The acts are performed in the order shown (e.g., top to bottom) or other orders. Certain acts may be omitted or changed depending on the results of the previous acts and the status of the patient.

At act A210, the image processor 22 acquires training data including unlabeled MR data, a predicted segmentation mask 301 generated by a trained segmentation network, a voxel level uncertainty map 303, and a lesion level uncertainty map 305. The training data also includes ground truth segmentation quality labels that describe the quality of the segmentation mask 301 generated by the trained segmentation network. The MR data represents the original image or volume that is input in the trained segmentation network. In an embodiment, the training data that is used to train the segmentation network may be used to train the network to generate the image level uncertainty measures. For example, the segmentation network may be trained using a set of training data and ground truth segmentation data. The same set of training data may be used as input to the trained segmentation network with the output used as inputs into the network that generates the image level uncertainty measures. In this scenario, the training data may also include ground truth uncertainty measures. In an alternative, a holdout set may be used.

In an embodiment, the voxel level measures 303 and lesion level measures 305 are generated by the image processor 22 from segmentation masks 301 generated by the trained segmentation network. The image processor 22 estimates voxel level measures 303 of uncertainty by performing MC dropout. The voxel level measures 303 may include estimates and/or values for each voxel in the segmented MR data. The collection of voxel level measures 303 may be stored or visualized as a voxel feature map. Maximum SoftMax probability or mutual information may also be used for estimating voxel level uncertainty. The image processor 22 may also generate the lesion level uncertainty values from the voxel level values of uncertainty. The estimated voxel level uncertainty measures are merged into lesion level uncertainty measures by taking the log-sum of voxel level uncertainties. The lesion level measures may include estimates and/or values for each identified lesion in the segmented MR data. The collection of lesion level measures may be stored or visualized as a lesion feature map.

In an embodiment, the image processor 22 increases the information density of the segmented lesion mask 301, the voxel level measures 303 of uncertainty, and the lesion level measures of uncertainty. In an embodiment, the image processor 22 increases the information density by EDT for the lesion mask 301 and by GDT for the voxel level and lesion level uncertainties. A distance map is an image where the value of each pixel is the distance from this pixel to the nearest pixel belonging to a given set or object. A distance transformation is an algorithm that computes a distance map from a binary image representing this set of pixels using a particular metric (e.g. Euclidean or Geodesic or others).

At act A220, the training data is used to train a network. As described above, the network may be a neural network such as CNN or DBN but other deep networks may be used. Alternative network arrangements may be used, for example, a 3D-VGGNet. Various units or layers may be used in the network, such as convolutional, pooling (e.g., max-pooling), deconvolutional, fully connected, or other types of layers. Within a unit or layer, any number of nodes is provided. For example, 100 nodes are provided. Later or subsequent units may have more, fewer, or the same number of nodes. In general, for convolution, subsequent units have more abstraction. For example, the first unit provides features from the image, such as one node or feature being a line found in the image. The next unit combines lines, so that one of the nodes is a corner. The next unit may combine features (e.g., the corner and length of lines) from a previous unit so that the node provides a shape indication. For transposed-convolution to reconstruct, the level of abstraction reverses. Each unit or layer reduces the level of abstraction or compression.

At act A230, the network outputs a segmentation performance metric that is compared against a ground truth performance metric at act A240. At act A250 the network is adjusted as a function of the comparison. The process of training may be repeated over and over until the network converges. At act A260, a trained network is output.

Figure 6:
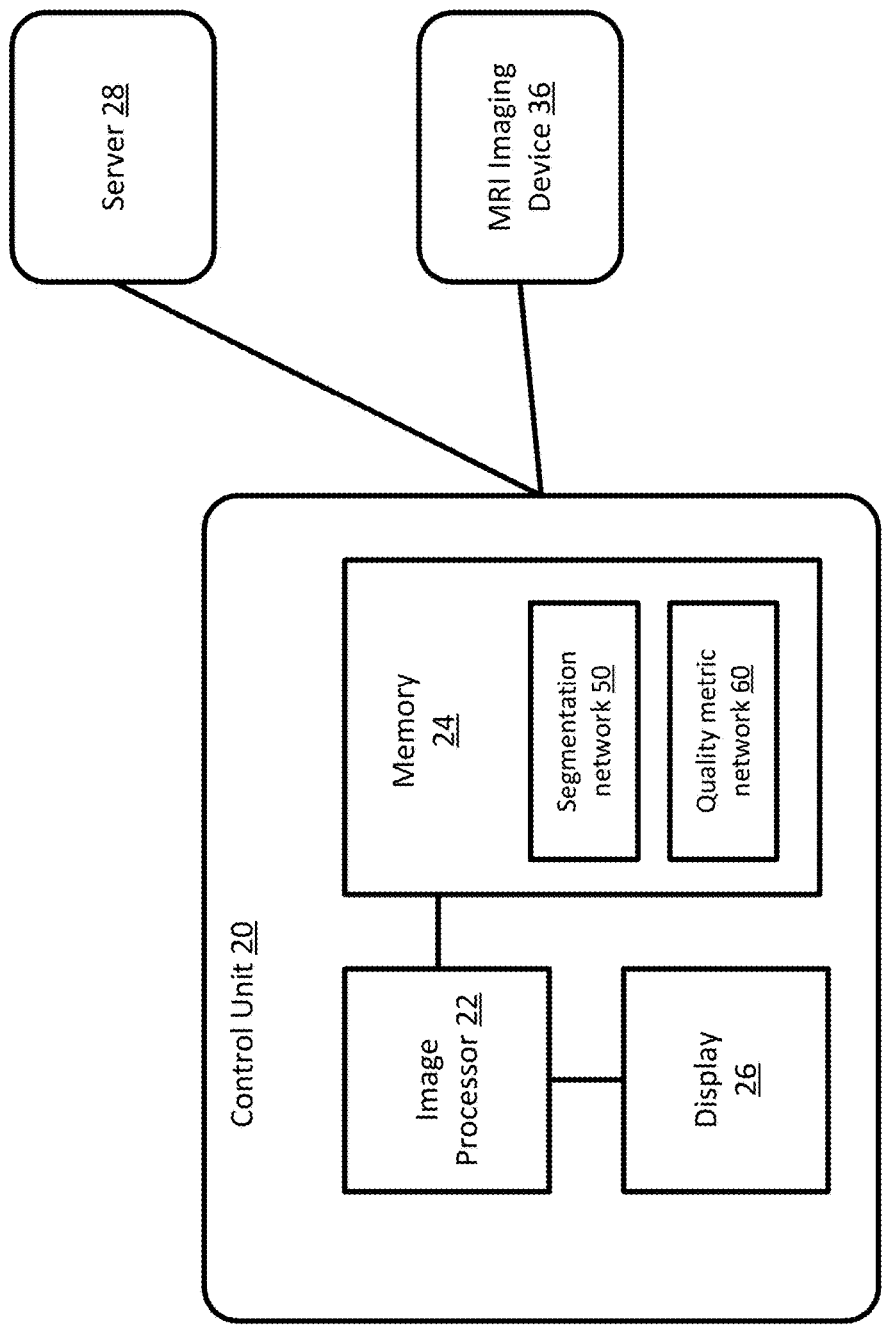
FIG. 6 depicts an example system for generating estimated uncertainty measures for lesion segmentation.

FIG. 6 depicts one embodiment of a control system 20 for automatically generating uncertainty measures for segmentation. The control system 20 includes an image processor 22, a memory 24, and a display 26. The control system 20 may be connected with a server 28 and an MR imaging device 36. Additional, different, or fewer components may be provided. For example, network connections or interfaces may be provided, such as for networking between the control system 20 and server 28. A workstation with a user interface may be provided for an operator to input data.

The MR imaging device 36 may be similar to the MR imaging device 36 as depicted in FIG. 1. The MR imaging device 36 is configured to acquire MR data that may be processed into one or more images or volumes by the control unit 20. The control unit 20 may provide commands to the MR imaging device 36. Alternatively, the MR imaging device 36 may function entirely on its own without any input from the control unit 20.

The image processor 22 (or processor) is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for processing an image. The processor 22 is a single device or multiple devices operating in serial, parallel, or separately. The processor 22 may be a main processor of a computer, such as a laptop or desktop computer, or may be a processor for handling some tasks in a larger system, such as in the MR system. The processor 22 is configured by instructions, design, hardware, and/or software to perform the acts discussed herein.

The server 28 may be co-located with the control unit 20 or may be located remotely. The server 28 may connect to the MR system 100 or control unit 20 via a network. The network is a local area, wide area, enterprise, another network, or combinations thereof. In one embodiment, the network is, at least in part, the Internet. Using TCP/IP communications, the network provides for communication between the processor 24 and the server 28. Any format for communications may be used. In other embodiments, dedicated or direct communication is used.

The server 28 may include the processor 24 or group of processors. More than one server 28 or control unit 20 may be provided. The server 28 is configured by hardware and/or software. The processor 24 and/or server 28 are configured to perform the acts discussed above for automated acquisition workflow. The processor 24 and/or server 28 may access and implement the code stored in memory 24.

The memory 24 may be a graphics processing memory, a video random access memory, a random-access memory, system memory, cache memory, hard drive, optical media, magnetic media, flash drive, buffer, database, combinations thereof, or other now known or later developed memory device for storing data or video information. The memory 24 is part of the control unit 20, part of a database, part of another system, a picture archival memory, or a standalone device. The memory 24 may store MR data from the MR device 36. The memory may store instructions or computer code for implementing a segmentation network 50 and a quality metric network 60.

The memory 24 includes an instruction set or computer code for implementing automated acquisition of medical imaging data. The memory 24 includes instructions for estimating uncertainty measurement on lesion segmentation. The memory 24 includes instructions for a network 50 that is configured to receive training data and to be trained to segment focal MS lesion. The segmentation network 50 may be any architecture such as a U-net. The trained segmentation network 50 is used to estimate voxel-level measures of uncertainty by performing MC dropout. The estimated voxel level uncertainty measures are merged into lesion-level uncertainty measures by taking the log-sum of voxel level uncertainties. The memory 24 includes instructions for a network 60 that is configured to receive input images, lesion mask(s) 301, voxel- and lesion-level uncertainty maps 303, 305 as input training data, and to be trained with a segmentation performance metric such as DICE similarity score to predict an image level uncertainty measure on a segmented lesion mask 301 that is produced by the segmentation network 50.

The memory 24 may store instructions and or data for one or more networks. The memory 24 includes instructions to increase the information density of the lesion mask 301, the voxel level uncertainties, and the lesion level uncertainties.

The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone, or in combination. Likewise, processing strategies may include multiprocessing, multitasking, parallel processing, and the like.

The display 26 may be configured to display images to an operator. The display 26 may augment the images with additional information or overlays. The display 26 may be configured to display the images in two dimensions, three dimensions, or, for example, in augmented or virtual reality scenarios.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method for estimating uncertainty measurements on lesion segmentation, the method comprising:
    acquiring, by a magnetic resonance imaging (MRI) device, MRI data for a patient;
    generating, using a first trained network, segmented lesion data from the MRI data;
    estimating, by an image processor, voxel level measures of uncertainty from the segmented lesion data;
    generating, by the image processor, lesion level measures of uncertainty from the voxel level measures of uncertainty; and
    predicting, by a second trained network, an image level uncertainty measure for the segmented lesion data, the second trained network configured to receive the MRI data, the segmented lesion data, the voxel level measures of uncertainty, and the lesion level measures of uncertainty as input data and to predict the image level uncertainty measure.

2. The method of claim 1, further comprising:
    increasing, by the image processor, information density of the segmented lesion data, the voxel level measures of uncertainty, and the lesion level measures of uncertainty.

3. The method of claim 2, wherein increasing information density comprises:
    increasing, by the image processor, information density by Euclidean distance transform for the segmented lesion data; and
    increasing, by the image processor, information density by geodesic distance transform for the voxel level measures of uncertainty and the lesion level measures of uncertainty.

4. The method of claim 1, wherein generating the lesion level measures of uncertainty comprises merging the voxel level measures of uncertainty into lesion level measures of uncertainty by taking the log-sum of the voxel level measures of uncertainty.

5. The method of claim 1, wherein estimating voxel level measure of uncertainty utilizes MC dropout.

6. The method of claim 1, wherein estimating voxel level measures of uncertainty utilizes maximum soft-max probability.

7. The method of claim 1, wherein the first trained network is a convolutional neural network trained to perform segmentation on input data.

8. The method of claim 1, wherein the second trained network trained using the same training data set as the first trained network.

9. The method of claim 1, further comprising:
    providing the image level uncertainty measure to inform a clinician of segmentation results that require further revision.

10. A method for training a network for predicting image level uncertainty, the method comprising:
    acquiring training data comprising an input image, a predicted segmentation mask generated by a trained segmentation network, a voxel level uncertainty map, and a lesion level uncertainty map;
    inputting the training data into the network;
    outputting a segmentation performance metric;
    comparing the segmentation performance metric against a ground truth performance metric;
    adjusting weights in the network as a function of the comparison; and
    outputting a trained network.

11. The method of claim 10, wherein inputting, outputting, comparing, and adjusting are repeated multiple times until convergence of a gradient to a solution.

12. The method of claim 10, wherein the segmentation network is trained using the training data.

13. The method of claim 10, further comprising:
    increasing the information density of the predicted segmentation mask, the voxel level uncertainty map, and the lesion level uncertainty map prior to inputting the training data into the network.

14. The method of claim 10, wherein the network is a convolutional neural network.

15. A system for predicting image level uncertainty, the system comprising:
    a trained segmentation network configured to input MRI data and output segmented lesion data;
    an image processor configured to generate a voxel level uncertainty map, and a lesion level uncertainty map from the segmented lesion data; and
    a trained network configured to receive the segmented lesion data, the input MRI data, the voxel level uncertainty map, and the lesion level uncertainty map and to predict an image level uncertainty measure.

16. The system of claim 15, further comprising:
    a display configured to present the image level uncertainty measure.

17. The system of claim 15, wherein the image processor is further configured to increase the information density of the voxel level uncertainty map, the lesion level uncertainty map, and the segmented lesion data.

18. The system of claim 15, wherein the trained network is a convolutional neural network.

19. The system of claim 15, wherein the image processor is configured to generate the voxel level uncertainty map from the segmented lesion data using Monte Carlo dropout.

20. The system of claim 15, wherein the image processor is configured to generate the lesion level uncertainty map from the voxel level uncertainty map using a log-sum algorithm.

* * * * *